United States Patent
Mayumi et al.

(10) Patent No.: US 7,179,891 B2
(45) Date of Patent: Feb. 20, 2007

(54) PHYSIOLOGICALLY ACTIVE COMPLEX

(75) Inventors: Tadanori Mayumi, 11-3, Ishibashi 3-chome, Ikeda-shi, Osaka (JP); Yasuo Tsutsumi, 2-20-503, Aomatani-nishi 4-chome, Minoo-shi, Osaka (JP); Shinsaku Nakagawa, 4-1, Nishikinomoto 4-chome, Yao-shi, Osaka (JP); Hakuo Ikegami, Okayama (JP)

(73) Assignees: Tadanori Mayumi, Osaka (JP); Yasuo Tsutsumi, Osaka (JP); Shinsaku Nakagawa, Osaka (JP); Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 552 days.

(21) Appl. No.: 10/668,178

(22) Filed: Sep. 24, 2003

(65) Prior Publication Data

US 2005/0013795 A1 Jan. 20, 2005

Related U.S. Application Data

(63) Continuation-in-part of application No. 10/354,985, filed on Jan. 31, 2003, now abandoned.

(30) Foreign Application Priority Data

Mar. 25, 2002 (JP) .............................. 2002-083509
Jun. 26, 2002 (JP) .............................. 2002-185387

(51) Int. Cl.
*C01K 1/00* (2006.01)
*A61K 45/00* (2006.01)

(52) U.S. Cl. ..................................... 530/351; 424/85.1

(58) Field of Classification Search ..................... None
See application file for complete search history.

(56) References Cited

U.S. PATENT DOCUMENTS

| 4,495,282 | A | | 1/1985 | Ohnishi et al. |
| 5,597,899 | A | | 1/1997 | Banner et al. |
| 5,773,582 | A | * | 6/1998 | Shin et al. ................... 530/351 |
| 6,541,224 | B2 | | 4/2003 | Yu et al. |

FOREIGN PATENT DOCUMENTS

| JP | 62-45208 | 9/1987 |
| JP | 62-289522 | 12/1987 |
| JP | 4-46928 | 7/1992 |

OTHER PUBLICATIONS

Terlikowski et al., Toxicology 2002, 174: 143-152.*

(Continued)

*Primary Examiner*—Larry R. Helms
*Assistant Examiner*—Hong Sang
(74) *Attorney, Agent, or Firm*—Browdy and Neimark, PLLC

(57) ABSTRACT

Disclosed is a physiologically active complex which comprises a proteinaceous part with TNF activity and a high molecular part bound artificially to the N-terminus of the proteinaceous part. The proteinaceous part in the complex has the amino acid sequence of SEQ ID NO:2 where Xaa is a member selected from the group consisting of asparagine, alanine, arginine, serine, threonine, proline, methionine, and leucine; while the high molecular part in the complex is a homopolymer of polyethylene glycol, copolymer of polyethylene glycol, or a derivative thereof.

5 Claims, 2 Drawing Sheets

OTHER PUBLICATIONS

Haranaka et al., "Antitumor Activity of Murine Tumor Necrosis Factor TNF) Against Transplanted Murine Tumors and Heterotranplanted Human Tumors in Nude Mice", *Int. J. Cancer*, vol. 34, pp. 263-267 (1984).

Tracey, "Chapter 16: Tumor necrosis Factor-Alpha", in *the Cytokine Handbook*, ed. Thomson, Academic Press, pp. 289-304 (1994).

* cited by examiner

SEQUENCE LISTING

<160> NUMBER OF SEQ ID NOS: 16

<210> SEQ ID NO 1
<211> LENGTH: 157
<212> TYPE: PRT
<213> ORGANISM: Homo sapiens

<400> SEQUENCE: 1

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 2
<211> LENGTH: 157
<212> TYPE: PRT
<213> ORGANISM: Artificial
<220> FEATURE:
<223> OTHER INFORMATION: synthetic (Variant protein of human tumor
      necrosis factor)
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:

```
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid

<400> SEQUENCE: 2

Val Arg Ser Ser Ser Arg Thr Pro Ser Asp Xaa Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Xaa Gly Gln Gly Cys Pro Ser Thr His Val Leu Leu Thr His Thr Ile
65                  70                  75                  80

Ser Arg Ile Ala Val Ser Tyr Gln Thr Xaa Val Asn Leu Leu Ser Ala
                85                  90                  95

Ile Xaa Ser Pro Cys Gln Arg Glu Thr Pro Glu Gly Ala Glu Ala Xaa
            100                 105                 110

Pro Trp Tyr Glu Pro Ile Tyr Leu Gly Gly Val Phe Gln Leu Glu Xaa
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 3
<211> LENGTH: 157
<212> TYPE: PRT
<213> ORGANISM: Artificial
<220> FEATURE:
<223> OTHER INFORMATION: synthetic (Variant protein of human tumor
      necrosis factor)

<400> SEQUENCE: 3

Val Arg Ser Ser Ser Arg Thr Pro Ser Asp Met Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80

Ser Arg Ile Ala Val Ser Tyr Gln Thr Pro Val Asn Leu Leu Ser Ala
                85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125
```

Gly Asp Arg Leu Ser Ala Glu Ile Asn Arg Pro Asp Tyr Leu Asp Phe
            130                 135                 140

Ala Glu Ser Gly Gln Val Tyr Phe Gly Ile Ile Ala Leu
145                 150                 155

<210> SEQ ID NO 4
<211> LENGTH: 92
<212> TYPE: DNA
<213> ORGANISM: Artificial
<220> FEATURE:
<223> OTHER INFORMATION: synthetic (Oligonucleotide used as primer with
      NNS sequence)
<220> FEATURE:
<221> NAME/KEY: misc_feature
<222> LOCATION: (21)..(22)
<223> OTHER INFORMATION: n is a, c, g, or t

<400> SEQUENCE: 4
tctactccca ggtcctcttc nnsggccaag gctgcccctc acccatgtg ctcctcaccc      60 acaccatcag ccgcatcgcc gtctcctacc ag                                   92

<210> SEQ ID NO 5
<211> LENGTH: 90
<212> TYPE: DNA
<213> ORGANISM: Artificial
<220> FEATURE:
<223> OTHER INFORMATION: synthetic (Oligonucleotide used as primer with
      NNS sequence)
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t

<400> SEQUENCE: 5
ggcctcagcc ccctctgggg tctccctctg gcaggggcts nngatggcag agaggaggtt      60
gacsnnggtc tggtaggaga cggcgatgcg                                       90

<210> SEQ ID NO 6
<211> LENGTH: 110
<212> TYPE: DNA
<213> ORGANISM: Artificial
<220> FEATURE:
<223> OTHER INFORMATION: synthetic (Oligonucleotide used as primer with
      NNS sequence)
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (88)..(89)
<223> OTHER INFORMATION: n is a, c, g, or t

<400> SEQUENCE: 6
tagtcgggcc gattgatctc agcgctgagt cggtcaccsn nctccagctg gaagacccct      60
cccagataga tgggctcata ccagggsnng gcctcagccc cctctgggt                110

<210> SEQ ID NO 7
<211> LENGTH: 95
<212> TYPE: DNA
<213> ORGANISM: Artificial
<220> FEATURE:
<223> OTHER INFORMATION: synthetic (Oligonucleotide used as primer with
      NNS sequence)

```
<220> FEATURE:
<221> NAME/KEY: misc_feature
<222> LOCATION: (72)..(73)
<223> OTHER INFORMATION: n is a, c, g, or t

<400> SEQUENCE: 7
tagttgttcc tttctatgcg gcccagccgg ccatggccat ggtcagatca tcttctcgaa      60
ccccgagtga cnnscctgta gcccatgttg tagca                                 95

<210> SEQ ID NO 8
<211> LENGTH: 49
<212> TYPE: DNA
<213> ORGANISM: Artificial
<220> FEATURE:
<223> OTHER INFORMATION: synthetic (Oligonucleotide used as primer with
      NNS sequence)

<400> SEQUENCE: 8
gcccagactc ggcaaagtcg agatagtcgg gccgattgat ctcagcgct                  49

<210> SEQ ID NO 9
<211> LENGTH: 36
<212> TYPE: DNA
<213> ORGANISM: Artificial
<220> FEATURE:
<223> OTHER INFORMATION: synthetic (Oligonucleotide used as primer with
      NNS sequence)

<400> SEQUENCE: 9
gttgttcctt tctatgcggc ccagccggcc atggcc                                36

<210> SEQ ID NO 10
<211> LENGTH: 58
<212> TYPE: DNA
<213> ORGANISM: Artificial
<220> FEATURE:
<223> OTHER INFORMATION: synthetic (Oligonucleotide used as linker to
      insert into an expression vector a cDNA coding a variant protein
      of human tumor necrosis factor)

<400> SEQUENCE: 10
gtttaacttt aagaaggaga tatacatatg gtcagatcat cttctcgaac cccgagtg        58

<210> SEQ ID NO 11
<211> LENGTH: 59
<212> TYPE: DNA
<213> ORGANISM: Artificial
<220> FEATURE:
<223> OTHER INFORMATION: synthetic (Oligonucleotide used as linker to
      insert into an expression vector a cDNA coding a variant protein
      of human tumor necrosis factor)

<400> SEQUENCE: 11
cttcctttcg ggctttgtta gcagccgaat tccagggcaa tgatcccaaa gtagacctg       59

<210> SEQ ID NO 12
<211> LENGTH: 471
<212> TYPE: DNA
<213> ORGANISM: Artificial
<220> FEATURE:
<223> OTHER INFORMATION: synthetic (DNA coding a variant protein of
      human tumor necrosis factor)
<220> FEATURE:
<221> NAME/KEY: CDS
<222> LOCATION: (1)..(471)

<400> SEQUENCE: 12
```

```
gtc aga tca tct tct cga acc ccg agt gac atg cct gta gcc cat gtt      48
Val Arg Ser Ser Ser Arg Thr Pro Ser Asp Met Pro Val Ala His Val
 1               5                  10                  15 gta gca aac cct caa gct gag ggg cag ctc cag tgg ctg aac cgc cgg      96
Val Ala Asn Pro Gln Ala Glu Gly Gln Leu Gln Trp Leu Asn Arg Arg
             20                  25                  30 gcc aat gcc ctc ctg gcc aat ggc gtg gag ctg aga gat aac cag ctg     144
Ala Asn Ala Leu Leu Ala Asn Gly Val Glu Leu Arg Asp Asn Gln Leu
         35                  40                  45 gtg gtg cca tca gag ggc ctg tac ctc atc tac tcc cag gtc ctc ttc     192
Val Val Pro Ser Glu Gly Leu Tyr Leu Ile Tyr Ser Gln Val Leu Phe
     50                  55                  60 tcg ggc caa ggc tgc ccc tcc acc cat gtg ctc ctc acc cac acc atc     240
Ser Gly Gln Gly Cys Pro Ser Thr His Val Leu Leu Thr His Thr Ile
 65                  70                  75                  80 agc cgc atc gcc gtc tcc tac cag acc ccc gtc aac ctc ctc tct gcc     288
Ser Arg Ile Ala Val Ser Tyr Gln Thr Pro Val Asn Leu Leu Ser Ala
                 85                  90                  95 atc cgc agc ccc tgc cag agg gag acc cca gag ggg gct gag gcc aac     336
Ile Arg Ser Pro Cys Gln Arg Glu Thr Pro Glu Gly Ala Glu Ala Asn
            100                 105                 110 ccc tgg tat gag ccc atc tat ctg gga ggg gtc ttc cag ctg gag ccg     384
Pro Trp Tyr Glu Pro Ile Tyr Leu Gly Gly Val Phe Gln Leu Glu Pro
        115                 120                 125 ggt gac cga ctc agc gct gag atc aat cgg ccc gac tat ctc gac ttt     432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                 471
Ala Glu Ser Gly Gln Val Tyr Phe Gly Ile Ile Ala Leu
145                 150                 155
```

<210> SEQ ID NO 13
<211> LENGTH: 157
<212> TYPE: PRT
<213> ORGANISM: Artificial
<220> FEATURE:
<223> OTHER INFORMATION: Synthetic Construct

<400> SEQUENCE: 13

```
Val Arg Ser Ser Ser Arg Thr Pro Ser Asp Met Pro Val Ala His Val
 1               5                  10                  15

Val Ala Asn Pro Gln Ala Glu Gly Gln Leu Gln Trp Leu Asn Arg Arg
             20                  25                  30

Ala Asn Ala Leu Leu Ala Asn Gly Val Glu Leu Arg Asp Asn Gln Leu
         35                  40                  45

Val Val Pro Ser Glu Gly Leu Tyr Leu Ile Tyr Ser Gln Val Leu Phe
     50                  55                  60

Ser Gly Gln Gly Cys Pro Ser Thr His Val Leu Leu Thr His Thr Ile
 65                  70                  75                  80

Ser Arg Ile Ala Val Ser Tyr Gln Thr Pro Val Asn Leu Leu Ser Ala
                 85                  90                  95

Ile Arg Ser Pro Cys Gln Arg Glu Thr Pro Glu Gly Ala Glu Ala Asn
            100                 105                 110

Pro Trp Tyr Glu Pro Ile Tyr Leu Gly Gly Val Phe Gln Leu Glu Pro
        115                 120                 125

Gly Asp Arg Leu Ser Ala Glu Ile Asn Arg Pro Asp Tyr Leu Asp Phe
130                 135                 140

Ala Glu Ser Gly Gln Val Tyr Phe Gly Ile Ile Ala Leu
145                 150                 155
```

<210> SEQ ID NO 14
<211> LENGTH: 471
<212> TYPE: DNA
<213> ORGANISM: Artificial
<220> FEATURE:
<223> OTHER INFORMATION: synthetic (DNA coding a variant protein of human tumor necrosis factor)
<220> FEATURE:
<221> NAME/KEY: CDS
<222> LOCATION: (1)..(471)

<400> SEQUENCE: 14

```
gtc aga tca tct tct cga acc ccg agt gac gcg cct gta gcc cat gtt     48
Val Arg Ser Ser Ser Arg Thr Pro Ser Asp Ala Pro Val Ala His Val
1               5                   10                  15 gta gca aac cct caa gct gag ggg cag ctc cag tgg ctg aac cgc cgg     96
Val Ala Asn Pro Gln Ala Glu Gly Gln Leu Gln Trp Leu Asn Arg Arg
                20                  25                  30 gcc aat gcc ctc ctg gcc aat ggc gtg gag ctg aga gat aac cag ctg    144
Ala Asn Ala Leu Leu Ala Asn Gly Val Glu Leu Arg Asp Asn Gln Leu
            35                  40                  45 gtg gtg cca tca gag ggc ctg tac ctc atc tac tcc cag gtc ctc ttc    192
Val Val Pro Ser Glu Gly Leu Tyr Leu Ile Tyr Ser Gln Val Leu Phe
    50                  55                  60 tcg ggc caa ggc tgc ccc tcc acc cat gtg ctc ctc acc cac acc atc    240
Ser Gly Gln Gly Cys Pro Ser Thr His Val Leu Leu Thr His Thr Ile
65                  70                  75                  80 agc cgc atc gcc gtc tcc tac cag acc cgc gtc aac ctc ctc tct gcc    288
Ser Arg Ile Ala Val Ser Tyr Gln Thr Arg Val Asn Leu Leu Ser Ala
                85                  90                  95 atc gcc agc ccc tgc cag agg gag acc cca gag ggg gct gag gcc ctc    336
Ile Ala Ser Pro Cys Gln Arg Glu Thr Pro Glu Gly Ala Glu Ala Leu
            100                 105                 110 ccc tgg tat gag ccc atc tat ctg gga ggg gtc ttc cag ctg gag acc    384
Pro Trp Tyr Glu Pro Ile Tyr Leu Gly Gly Val Phe Gln Leu Glu Thr
        115                 120                 125 ggt gac cga ctc agc gct gag atc aat cgg ccc gac tat ctc gac ttt    432
Gly Asp Arg Leu Ser Ala Glu Ile Asn Arg Pro Asp Tyr Leu Asp Phe
130                 135                 140 gcc gag tct ggg cag gtc tac ttt ggg atc att gcc ctg                471
Ala Glu Ser Gly Gln Val Tyr Phe Gly Ile Ile Ala Leu
145                 150                 155
```

<210> SEQ ID NO 15
<211> LENGTH: 157
<212> TYPE: PRT
<213> ORGANISM: Artificial
<220> FEATURE:
<223> OTHER INFORMATION: Synthetic Construct

<400> SEQUENCE: 15

```
Val Arg Ser Ser Ser Arg Thr Pro Ser Asp Ala Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
    50                  55                  60

Ser Gly Gln Gly Cys Pro Ser Thr His Val Leu Leu Thr His Thr Ile
65                  70                  75                  80
```

```
Ser Arg Ile Ala Val Ser Tyr Gln Thr Arg Val Asn Leu Leu Ser Ala
                85              90              95

Ile Ala Ser Pro Cys Gln Arg Glu Thr Pro Glu Gly Ala Glu Ala Leu
            100             105             110

Pro Trp Tyr Glu Pro Ile Tyr Leu Gly Gly Val Phe Gln Leu Glu Thr
        115             120             125

Gly Asp Arg Leu Ser Ala Glu Ile Asn Arg Pro Asp Tyr Leu Asp Phe
        130             135             140

Ala Glu Ser Gly Gln Val Tyr Phe Gly Ile Ile Ala Leu
145             150             155

<210> SEQ ID NO 16
<211> LENGTH: 157
<212> TYPE: PRT
<213> ORGANISM: Artificial
<220> FEATURE:
<223> OTHER INFORMATION: synthetic (Variant protein of human tumor
      necrosis factor)

<400> SEQUENCE: 16

Val Arg Ser Ser Ser Arg Thr Pro Ser Asp Ala Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Ser Gly Gln Gly Cys Pro Ser Thr His Val Leu Leu Thr His Thr Ile
65              70                  75                  80

Ser Arg Ile Ala Val Ser Tyr Gln Thr Arg Val Asn Leu Leu Ser Ala
                85              90              95

Ile Ala Ser Pro Cys Gln Arg Glu Thr Pro Glu Gly Ala Glu Ala Leu
            100             105             110

Pro Trp Tyr Glu Pro Ile Tyr Leu Gly Gly Val Phe Gln Leu Glu Thr
        115             120             125

Gly Asp Arg Leu Ser Ala Glu Ile Asn Arg Pro Asp Tyr Leu Asp Phe
        130             135             140

Ala Glu Ser Gly Gln Val Tyr Phe Gly Ile Ile Ala Leu
145             150             155
```

PHYSIOLOGICALLY ACTIVE COMPLEX

CROSS-REFERENCE TO RELATED APPROCATIONS

This application is a continuation-in-part of: application Ser. No. 10/354,985 filed Jan. 31, 2003, now abandoned. The above-identified application for which the present application is a continuation-in-part is incorporated entirely herein by reference.

BACKGROUND OF THE INVENTION

1. Field of the Invention

The present invention relates to a novel physiologically active substance, more particularly, to a physiologically active complex having an activity of tumor necrosis factor (abbreviated as TNF hereinafter).

2. Description of the Prior Art

As described in "*The Cytokine Handbook*", 2nd edition, edited by Angus Thomson, published by Academic Press, pp. 289–304 (1994) TNF was first discovered by L. J. Old et al. in 1975 as a cytotoxic factor secreted in serum of animals such as rabbits and mice when sequentially administered with BCG and bacterial toxin. Later studies revealed that TNF is a protein having a molecular weight of about 17,000 daltons and an isoelectric point of 5.6, produced mainly by macrophages.

From the beginning of the discovery, TNF has been highly focused on its use as a medicament for malignant tumors and developed for such purposes due to its selective cytotoxic action on tumor cells, as disclosed in Japanese Patent Kokoku Nos. 45,208/87 and 46,928/92. However, when intravenously administered to living bodies, TNF is promptly decomposed by protease in the blood or excreted into urine within a relatively short period of time so that TNF could not be kept at the desired blood level for a relatively long period of time. While, an increased amount of TNF administration to subjects to higher the blood level of TNF would affect even normal cells due to the cytotoxic action by TNF.

SUMMARY OF THE INVENTION

Under these circumstances, the present invention was made to provide a stable physiologically active substance which has TNF activity and improved dynamics in living bodies.

After energetic studies and screenings, the present inventors found that a physiologically active substance, which comprises both a proteinaceous part having TNF activity and a high molecular part bound artificially to the N-terminus of the proteinaceous part and which has a higher stability and a longer retention time in living bodies than intact TNF with no such a high molecular part. As a result, it was found that the blood level of TNF is kept at the desired level for a relatively long period of time even when administered at a lesser dose.

The present invention solved the above object by providing a physiologically active complex comprising both a proteinaceous part having TNF activity and a high molecular part bound artificially to the N-terminus of the proteinaceous part.

Also, the present invention solved the above object by providing an agent for susceptive diseases, comprising the above physiologically active complex as an effective ingredient.

BRIEF DESCRIPTION OF THE ACCOMPANYING DRAWINGS

DETAILED DESCRIPTION OF THE INVENTION

Figure 1:
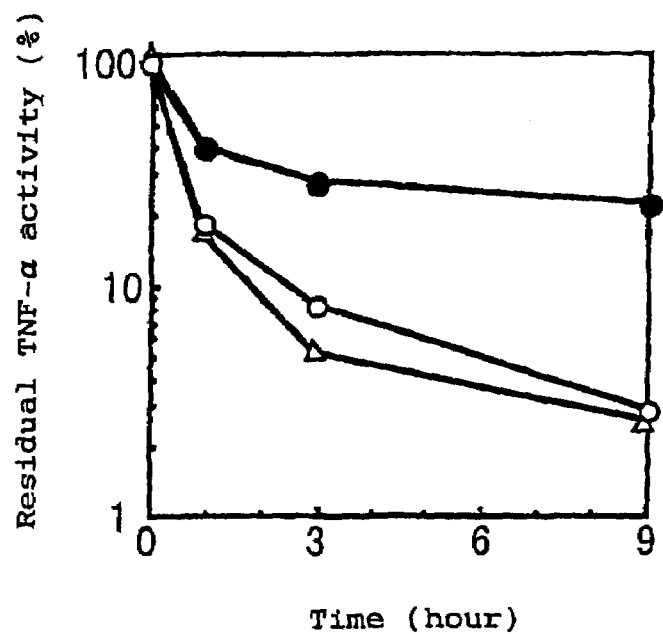
FIG. 1 shows the stability of the physiologically active complex of the present invention and a control substance in murine blood.

Now explaining the preferred embodiments according to the present invention, the physiologically active complex as referred to as in the present invention means a physiologically active complex comprising both a proteinaceous part having TNF activity and a high molecular part bound artificially to the N-terminus of the proteinaceous part. The proteinaceous part as a constituent of the physiologically active complex of the present invention can be obtained, for example, by the protein engineering technique: Among the amino acids which constitute TNF, amino acids such as lysine having a free amino group, excluding those which are positioned at the N-terminus of TNF, can be replaced with an amino acid with no free amino group, preferably, with any of asparagine, alanine, arginine, serine, threonine, proline, methionine, and leucine.

As it is well known, TNFs vary in amino acid sequences depending on their origins; human TNF consists of 157 amino acids represented by the amino acid sequence of SEQ ID NO:1. As concrete examples of the physiologically active complex to be incorporated into the later explained agent for susceptive diseases, those which comprise, as a proteinaceous part, the amino acid sequence of SEQ ID NO:2 where Xaa is a member selected from the group consisting of asparagine, alanine, arginine, serine, threonine, proline, methionine, and leucine; preferably, those which comprises the amino acid sequence of SEQ ID NO:3 as a proteinaceous part. The above proteins, where the 11th, 65th, 90th, 98th, 112th and 128th lysines in conventionally known human TNF are replaced with any of asparagine, alanine, arginine, serine, threonine, proline, methionine, and leucine, are different from the intact human TNF, however, they exert the same or higher cytotoxic action on tumors in general as compared with the human TNF.

As described above, these proteins can be obtained by the protein engineering technique in such a manner of replacing one or more amino acids as constituents of proteins with the desired amino acid(s). For example, libraries of DNAs encoding proteins, which the amino acids with a free amino group of TNF are replaced with a random amino acid(s), are obtained by subjecting to PCR reaction an oligonucleotide obtained by replacing with a NNS sequence a codon which encodes an amino acid having a free amino group corresponding to the DNA which encodes TNF; and then in the presence of the resulting PCR products the above DNA is subjected to PCR reaction to obtain a library of DNAs which encode proteins of modified TNFs which the amino acids with free amino groups in TNF are replaced with random amino acids. Thereafter, the DNAs in the library are allowed to express the proteins which they each encode by using the phage display method, etc., followed by applying conventional sequence analysis to the expressed proteins in combination with other techniques such as a solid phase enzyme immunoassay using anti-TNF antibodies, panning method using anti-TNF antibodies or TNF-receptor-proteins, and bioassay using target cells against TNF. Thus, DNAs encoding proteins, which the amino acids with free amino groups in TNF are replaced with amino acids with no free amino group except for the N-terminal amino acid of TNF, are obtained. To select the desired DNAs from the above DNAs, the phage display method is quite useful, and the combination use of the phage display method and one or more of the above techniques facilitates to smoothly and thoroughly select a series of proteins which the amino acids with free amino groups in TNF, except for the one at the N-terminus of TNF, are replaced with amino acids with no free amino group while retaining the desired TNF activity at a relatively high level.

The protein which constitutes the physiologically active complex of the present invention can be obtained in the desired amount by introducing the DNAs thus obtained directly or after amplified by PCR reaction into appropriate hosts such as *Escherichia coli* via plasmid vectors to transform the host cells, selecting a clone capable of producing the desired protein from the transformed cells, and culturing the selected clone to obtain the objective protein in the desired amount. To collect the produced protein from the culture of the transformant, conventional methods used in general for purifying proteins such as dialysis, salting out, filtration, concentration, centrifugation, separatory sedimentation, gel filtration chromatography, ion-exchange chromatography, hydrophobic chromatography, affinity chromatography, chromatofocusing, gel electrophoresis, and isoelectrophoresis can be used. These methods are appropriately used in combination.

The physiologically active complex of the present invention can be obtained by allowing to artificially bind a high molecular substance to the N-terminus of the protein having TNF activity. The high molecular substances usable in the present invention are those which are substantially water-soluble and unharmful to living bodies, more particularly, non-proteinaceous substances with lesser fear of acting as antigens in living bodies. Referring to the molecular form of the high molecular weight substances, those in a straight- or branched-form can be used, however, those in a branched form are preferable. Examples of such high molecular substances include homopolymers of polyvinyl alcohol, polyethylene glycol, polyvinylpyrrolidone, or polypropylene glycol; copolymers of ethylene glycol and vinyl alcohol or propylene glycol; and synthetic high molecular substances thereof; and natural high molecular substances such as elsinan, dextran, hydroxyethyl cellulose, pullulan, and methyl cellulose. Among these, homopolymers and copolymers of polyethylene glycol and derivatives thereof are preferable because they are easily available in the form of a relatively homogeneous molecular-size-distribution. The molecular weight of the high molecular substances can be usually increased or decreased within the range of 500–50,000 daltons, preferably, 1,000–10,000 daltons as an average molecular weight; and when the high molecular substances are inhomogeneous in their molecular weight, they should preferably be fractionated by conventional methods such as separation sedimentation and gel filtration chromatography prior to reaction. Depending on the kind of the high molecular substances used and the final use of the physiologically active complex, the high molecular substances with a lower molecular weight outside the above range may not substantially improve the in vivo dynamics of the complex, while those with a higher molecular weight outside the above range may lower the water solubility of the complex, and these would hinder the safe use of the complex as a pharmaceutical.

To bind the above high molecular substances to the N-terminus of the protein with TNF activity, a high molecular substance, which has been activated with a reagent that specifically acts on free amino groups to form a covalent bonding, is allowed to react with the protein; or a high molecular substance and the protein are cross-linked using a polyfunctional reagent having a functional group which specifically reacts with free amino groups. Examples of the reaction method include those which are commonly used in the art, for example, the ether bonding method as disclosed in Japanese Patent Kokai No. 289,522/87 and the amido bonding method; among these, the amido bonding method is preferable with respect to the stability of the covalent bonding formed between the proteins and the high molecular substances.

Varying depending on the reaction method used, the ratio of a protein and a high molecular substance employed in the initiation of reaction is increased or decreased within the range of 1:0.1 to 1:100, preferably, 1:0.5 to 1:50 (=(protein):(high molecular substance)) by molar ratio. In general, when the ratio is below the above range, proteins become to easily bind each other; while when the ratio is over the above range, high molecular substances become to easily bind each other. In any case, since the ratio outside the above preferable range will lower the reaction rate of the protein and the high molecular substance and decrease the purification efficiency of the reaction product, the ratio should preferably be increased or decreased within the above-identified range. The reaction temperature, pH, and time are set so as not to inactivate and decompose proteins with TNF activity and to minimize undesirable side reactions: The temperature is set to 0–100° C., preferably, 20–40° C.; the pH is set to 0.1–12, preferably, 5–9; and the time is set to terminate the reaction within 0.1–50 hours, preferably, within 10 hours. The physiologically active complex thus obtained can be purified by similar methods as used in purifying the proteins with TNF activity, and optionally further treated with concentration, salting out, centrifugation, lyophilization, etc., into products in a liquid or solid form, depending on final use.

The physiologically active complex of the present invention is useful as a medicament for treating and/or preventing susceptive diseases. The term "susceptive diseases" as referred to as in the present invention means diseases in general which can be treated and/or prevented by the administration of the physiologically active complex with or without other medicaments. Examples of such diseases include solid tumors such as colonic cancer, rectal cancer, gastric cancer, thyroid carcinoma, cancer of the tongue, bladder carcinoma, choriocarcinoma, hepatoma, carcinoma uteri, cancer of pharynx, lung cancer, breast cancer, malignant melanoma, neuroblastoma, pyo-ovarium, testicular tumor, osteosarcoma, pancreatic cancer, hypernephroma, goiter, brain tumor, and mycosis fungoides; hematopoietic tumors such as leukemia and lymphoma; and others such as viral diseases, bacterial diseases, and immunopathies. Thus, the agents for susceptive diseases of the present invention have a variety of uses as antitumor agents, antiviral diseases, anti-infectives, and agents for immunopathies which are used in treating and/or preventing the above diseases.

Varying depending on the types and the symptoms of susceptive diseases to be treated, the agent for susceptive diseases of the present invention is prepared to facilitate the administration of at least 0.1 ng/kg body weight per shot, preferably, 1–1,000 ng/kg body weight per shot of the physiologically active complex while varying the dose level depending on administration route; and is prepared into an extract, elixir, lower airway inhalation, capsule, granule, ophthalmic sustained-release-drug, pill, ophthalmic ointment, cataplasm for tunica mucosa oris, suspension, emulsion, plaster, suppository, powder, tablet, syrup, dipping agent, decoction, injection, tincture, eye-drop, eardrop, nasal drop, troche, ointment, cataplasm, aromatic water, nasal nebulas, liniment, limonade, fluidextract, lotion, etc.

The agent for susceptive diseases of the present invention includes those in a dosage unit form which contain, for example, an amount equal to a single dose or an integral multiple dose up to four times of the single dose, or to a division of the single dose up to 1/40 time thereof; and which are in the form of a physically separated systematic agent suitable for administration. Examples of such are capsules, granules, pills, suppositories, powders, tablets, injections, and cataplasms.

In addition to the physiologically active complex of the present invention as the effective ingredient, appropriate agents such as excipients, ointment bases, dissolving agents, corrigents, flavors, colors, a-and emulsifiers, which are commonly used in preparing medicaments, can be freely incorporated into the agent for susceptive diseases of the present invention. Within the scope of the object of the present invention, the physiologically active complex of the present invention can be used together with, as another effective ingredient, one or more other agents, for example, external dermal agents such as external dermal sterilizing and pasteurizing agents, would protecting agents, and antiphlogistics; vitamin preparations such as vitamin A, vitamin B, vitamin C, vitamin D, vitamin E, and vitamin K; calcium preparations; mineral preparations; saccharide preparations; organic acid preparations; protein and amino acid preparations; revitalizers such as organ preparations; chlorophyll preparations; cell activating preparations such as dye preparations; antitumor agents such as alkylating agents, antimetabolites, antitumor antibiotic preparations, and antitumor plant-ingredient preparations; allergic agents such as antihistamines; chemotherapeutics such as antituberculosis drugs, synthetic antimicrobial agents, and antiviral agents; and others such as hormone preparations, antibiotic preparations, and biological preparations.

The physiologically active complex of the present invention can be used in combination with the following antitumor agents as adjuvants to exert a synergistically high effect which could not be easily attained by their single use: Antitumor agents such as actinomycin D, aceglatone, irosfamide, ubenimex, etoposide, enocitabin, aclarubicin hydrochloride, idarubicin hydrochloride, irinotecan hydrochloride, epirubicin hydrochloride, gemcitabine hydrochloride, daunorubicin hydrochloride, doxorubicin hydrochloride, nitrogen mustard-N-oxide hydrochloride, nimustine hydrochloride, pirarubicin hydrochloride, bleomycin hydrochloride, procarbazine hydrochloride, mitoxantrone hydrochloride, carboquone, carboplatin, carmofur, tomoxifen citrate, toremifene, krestin, medroxyprogesterone acetate, cyclophosphamide, cisplatin, schizophyllan, cirarabine, citarabine ocfosfate, zinostantin stimalamer, vinonelbine ditartrate, sobuzoxane, dacarbazine, thiotepa, tegafur, tegafur uracil, tegafur gimesutat otastat potassium, doxifluridine, docetaxel hydrate, toretinoin, neocarzinostatin, nedaplatin, paclitaxel, bicalutamido, picibanyl, hydroxycarbamide, busulfan, fluorouracil, flutamido, pentostatin, porfimer sodium, mitomycin C, methotrexate, mercaptopurine, 6-mercaptopurine riboside, bleomycin sulfate, peplomycin sulfate, and lentinan. The above-mentioned combination use will reduce the dose of antitumor agents and effectively lower their side effects.

The agent for susceptive diseases of the present invention exerts therapeutic and/or prophylactic effects on the diseases independently of its oral or parenteral administration route. Depending on the types or symptoms of susceptive diseases to be treated, the agent is administered orally or parenterally such as intradermal, subcutaneous, intramuscular, intravenous, intranasal, rectal, and intraperitoneal routes, to a subject at a dose of 0.1 to 1,000 ng/day/kg body weight, preferably, 1 to 100 ng/day/kg body weight of the physiologically active complex, where the dose is optionally divided into several portions and the administration frequency is one to seven shots per week for one week to a half year. Since the physiologically active complex of the present invention is stable and hardly decomposed by protease in the blood and stays longer in living bodies than intact TNF by two times or more depending on its administration route, the dose can be significantly minimized when administered to a subject suffering from the same susceptive disease through the same administration route, resulting in a beneficial reduction of side effects inducible by the cytotoxicity of TNF against normal cells.

The following examples explain the preferred examples of the present invention:

EXAMPLE 1

Preparation of Protein with TNF Activity

According to conventional manner, the oligonucleotides represented by SEQ ID NOs:4 and 5 as primers were subjected to PCR reaction with Taq polymerase at 60° C. The reaction mixture was purified to obtain a PCR product consisting of 162 base pairs where the 65th, 90th and 98th lysines in human TNF represented by SEQ ID NO:1 were replaced with random amino acids. In the presence of the oligonucleotides as primers represented by SEQ ID NOs: 6 and 7, the above PCR product was further subjected to PCR reaction with Taq polymerase at 60° C., and then the reaction mixture was purified to collect a PCR product consisting of 251 base pairs where the 65th, 90th, 98th, 112th, and 128th lysines in human TNF represented by SEQ ID NO:1 were all replaced with random amino acids.

While, according to conventional manner, a DNA encoding human TNF represented by SEQ ID NO:1 was introduced into a phagemid vector, "pCantab5e", a trade name of and produced by Ammasham Biosciences, K. K. Tokyo, Japan. Using the resulting phagemid vector as a template, it was amplified with Accutaq DNA polymerase, in the presence of the above PCR product as a primer consisting of 251 base pairs and the oligonucleotides represented by SEQ ID NOs:8 and 9, to obtain a PCR fragment consisting of 463 base pairs where the 11th, 65th, 90th, 98th, 112th and 128th lysines in the amino acid sequence of SEQ ID NO:1 were all replaced with random amino acids. The PCR fragment thus obtained was introduced into a phagemid vector by conventional phage display method to obtain a phage library which expressed mutants of human TNF in which a part or the whole of the six lysines had been replaced with random amino acids. Panning method using a plasmon resonance apparatus, "BIACORE 2000", a trade name of and commercialized by Biacore K. K. Tokyo, Japan, which had an anti-TNF antibody immobilized on a sensor tip, was repeatedly applied to the above library to screen the desired clones capable of binding the antibody. Furthermore, a bioassay for cytotoxicity of the clones using L-M cells, ATCC CCL1.2, derived from a murine connective tissue, was applied to the screened clones to select the objective clones encoding a protein with TNF activity, revealing that proteins, where the 11th, 65th, 90th, 98th, 112th and 128th lysines in the amino acid sequence of SEQ ID NO:1 were replaced with any of asparagine, arginine, alanine, serine, threonine, proline, methionine, or leucine, had a relatively high TNF activity.

Using one of the clones encoding the above proteins, a part of a DNA encoding a protein with the highest possible TNF-activity was amplified in the presence of the oligonucleotides represented by SEQ ID NOs:10 and 11 as primers, and the resulting amplified DNA having the nucleotide sequence represented by SEQ ID NO:12 was introduced into a plasmid vector, "pUC18", a trade name of and produced by Takara Shuzo, Co., Ltd., Tokyo, Japan. Then, according to conventional manner, the resulting plasmid vector was introduced into BL21DE3 strain, a microorganism of the species *Escherichia coli*, followed by culturing the resulting transformant and then purifying the resulting culture using methods such as ion-exchange chromatography and gel filtration chromatography to collect a protein having the amino acid sequence represented by SEQ ID NO:3.

A part of the protein thus obtained was sampled and subjected to SDS-PAGE in the presence of 2-mercaptoethanol and revealed to have a main band at around 17,000 daltons. Measurement of free amino acid of the protein in this example by conventional fluorescamine method revealed that the protein had one free amino group per molecule. According to conventional manner, the cytotoxicity of the protein was assayed by a bioassay using L-M cells as a target cell and revealed that the $IC_{50}$ (a concentration of a sample which inhibits the survival of the target cell by 50%) of the protein was 0.23 ng/ml, substantially the same level as that of 0.22 ng/ml for a human recombinant TNF as a control. These results show that the protein in this example has a replacement of six lysines among the seven amino acids having free amino groups in TNF, excluding the amino acid at the N-terminus, with other amino acids having no free amino group, differs from TNF in several constituent amino acids of TNF, and exerts substantially the same level of cytotoxicity against target cells as that of TNF.

EXAMPLE 2

Preparation of Physiologically Active Complex

A protein having TNF activity, obtained by the method in Example 1, was dissolved in aqueous phosphate buffered saline (pH 8.5) to give a concentration of 0.1 to 1 mg/ml and admixed with methoxypolyethyleneglycol as a high molecular substance having an average molecular weight of 5,000 daltons, which had been activated by the addition of monomethoxypolyethyleneglycol-N-succinimidylpropionate in an amount of five times of the protein by molar ratio, followed by reacting the mixture at 37° C for 30 min. Thereafter, to the resulting mixture was added c-aminocaproic acid in an amount of 10-times of the high molecular substance by molar ratio and allowed to stand for a while before terminating the reaction. The reaction mixture was then purified by conventional method using gel filtration chromatography to obtain a homogeneous physiologically active complex in which polyethylene glycol bound to the N-terminus of a proteinaceous part of the complex and had substantially no nonuniformity in molecular level.

The complex thus obtained exhibited a main peak at around 24,000 daltons on SDS-PAGE in the presence of 2-mercaptoethanol. When assayed for cytotoxicity by the above method using L-M cells as a target cell, both the complex in this example and a recombinant human TNF had an $IC_{50}$ of 0.34 ng/ml, meaning that they had substantially the same level of cytotoxicity. While another preparation of physiologically active complex was prepared with polyethylene glycol similarly as above except for altering the average molecular weight of the polyethylene glycol to 40,000 daltons and tested for cytotoxicity against L-M cells similarly as above, revealing that the preparation had an $IC_{50}$ of 0.43 ng/ml and retained about 70% of the TNF activity of the control.

EXAMPLE 3

Antitumor Action

According to usual manner, BALB/c female mice (4-weeks-old, 20 g weight each), which had been inoculated with meth A cells, ATCC 63181, a murine sarcoma, were divided into groups consisting of three heads per group and then injected into their tail veins with a physiological saline containing a physiologically active complex obtained by the method in Example 2, a protein with TNF activity obtained by the method in Example 1, or a recombinant human TNF at the doses in Table 1. At 24 hours after the administrations, the mice were examined for occurrence of hemorrhagic necrosis and sudden death, and measured for diameter of tumors at prescribed time intervals, followed by calculating the tumor volume according to the method described by Keisuke Haranaka in *International Journal of Medicine*, Vol. 34, pp. 263–267 (1984). The antitumor effects (%) of the samples tested were calculated by comparing the tumor volumes of the mice, received with the samples, with those of the control mice injected with only physiological saline on day 20th after the transplantation of tumor cells. The results are in Table 1.

TABLE 1

| Sample | Dose (μg/head) | Sudden death (%) | Antitumor effect (%) |
|---|---|---|---|
| Recombinant human TNF | 10 | 100 | — |
|  | 3 | 0 | 10 |
| Protein obtained by | 10 | 100 | — |
| the method in Example 1 | 3 | 0 | 30 |
| Physiologically active | 10 | 0 | — |
| complex obtained by | 3 | 0 | 80 |
| the method in Example 2 | 1 | 0 | 30 |

Note:
In the table, the symbol "—" means that it was not experimented.

As evident from the results in the Table 1, the mice administered with either the protein obtained by the method in Example 1 or the recombinant human TNF were induced hemorrhagic necrosis within 24 hours after the administration at a dose of 10 μg/head, and all the mice died suddenly. When the dose of the protein or the recombinant human TNF was lowered stepwisely, the sudden death of mice could be avoided but no complete reduction of tumor mass was observed, and most of the mice died within 40 days after the administrations. While there were found no sudden death in the group administered with the physiologically active complex of the present invention even when administered at a dose of 10 μg/head, but found a significant antitumor effect even when administered at a dose of 3 μg/head. The data shows that the physiologically active complex of the present invention effectively elicits the antitumor effect of proteins having TNF activity and also significantly lowers the side effects of TNF.

EXAMPLE 4

In vivo Dynamics

A serum collected from BALB/c mice and a 3.3 μg/ml solution of a physiologically active complex, which had been obtained by the method in Example 2 and diluted with physiological saline, were mixed in a ratio of 3:1 by volume, and the mixture was incubated at 37° C. for nine hours while it was sampled at a prescribed time interval. The collected samples were instantly measured for cytotoxic activity using L-M cells as a target cell, followed by judging residual cytotoxicity as an index of the stability of the samples. In parallel, systems as controls, where a recombinant human TNF or a protein obtained by the method in Example 1 was administered to the target cell in place of the physiologically active complex, were respectively provided and treated similarly as above. The results are in FIG. 1. In FIG. 1, the systems administered with the physiologically active complex, the recombinant human TNF, and the protein obtained by the method in Example 1 were respectively expressed with the symbols "○", "●" and "Δ".

As found in FIG. 1, the recombinant human TNF and the protein in the control systems were easily decomposed, and their residual cytotoxic activities lowered to about three percent after 9-hours incubation. While the system with the physiologically active complex of the present invention still retained a residual cytotoxic activity of 20% or more even after 9-hours incubation. The data indicates that the physiologically active complex of the present invention is not substantially decomposed by protease, etc., in the blood, and stably remains therein.

Figure 2:
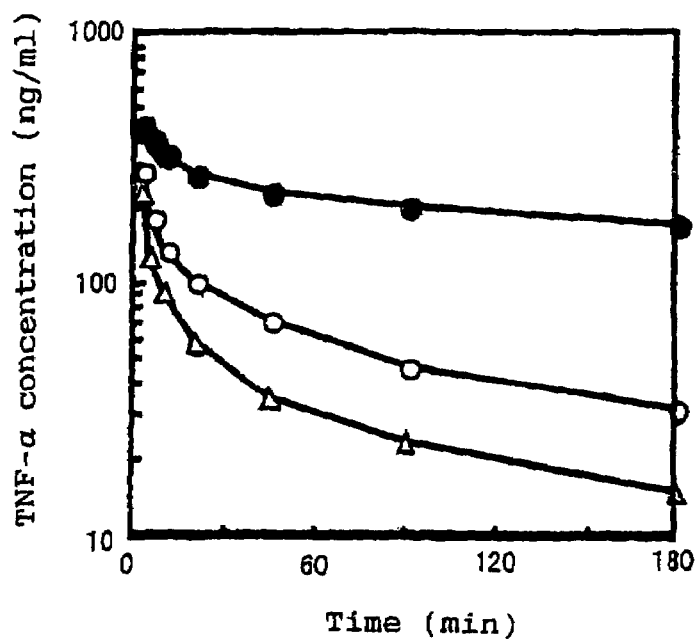
FIG. 2 shows in vivo dynamics of the physiologically active complex of the present invention in Example 2, containing a polypeptide having amino acid sequence described in SEQ ID NO:3 and a control substance.

The physiologically active complex obtained by the method in Example 2 was diluted with physiological saline to give a concentration of 5 μg/ml and injected into tail veins of BALB/c mice at a dose of 200 μl/head. Thereafter, the mice were sampled their blood at a prescribed time interval over three hours, and the serum level of the complex was assayed using a neutralizing antibody. In parallel, systems as controls, where a recombinant human TNF or a protein obtained by the method in Example 1 was administered to the target cell in place of the physiologically active complex, were respectively provided and treated similarly as above. The results are in FIG. 2. In FIG. 2, the systems administered with the physiologically active complex, the recombinant human TNF, and the protein obtained by the method in Example 1 were respectively expressed with the symbols "○", "●" and "Δ".

As evident from the results in FIG. 2, in the control systems, the serum levels of the recombinant human TNF and the protein instantly decreased just after the administrations and lowered to about 10% with respect to their initial levels. at three hours after the administrations. While the system with the physiologically active complex of the present invention still had a residual cytotoxic activity of at least 50% with respect to the initial level. The data indicates that the physiologically active complex of the present invention has superior in vivo dynamics and stays loner in living bodies as compared with conventional TNF and mutants thereof having no high molecular substance part at the N-terminus of TNF.

EXAMPLE 5

Acute Toxicity

According to conventional manner, mice aged eight weeks were percutaneously, orally, or peritoneally administered with the physiologically active complex of the present invention obtained by the method in Example 2, revealing that the $LD_{50}$ of the complex was 1 mg/kg body weight or more independently of its administration routes. This means that the physiologically active complex of the present invention can be incorporated into pharmaceuticals directed to be administered to humans with lesser side effects.

EXAMPLE 6

Liquid

A physiologically active complex, obtained by the method in Example 2, was dissolved in physiological saline containing one percent (w/w) of human serum albumin as a stabilizer to give a concentration of one milligram per milliliter, followed by filtering the solution with a membrane for sterilization in usual manner to obtain a liquid.

The product with a satisfactory stability is useful as an injection, ophthalmic solution, or nasal drop to treat and/or prevent susceptive diseases including malignant tumors, viral disease, bacterial infections, and immunopathies.

EXAMPLE 7

Dried Injection

One hundred milligrams of a physiologically active complex, obtained by the method in Example 2, was dissolved in 100 ml of physiological saline containing one percent (w/w) of a purified human gelatin as a stabilizer, and then the resulting solution was membrane filtered for sterilization in usual manner. One milliliter aliquots of the filtrate were distributed into vials and lyophilized, followed by sealing the vials to obtain a dried injection.

The product with a satisfactory stability is useful as an injection, ophthalmic solution, or nasal drop to treat and/or prevent susceptive diseases including malignant tumors, viral disease, bacterial infections, and immunopathies.

EXAMPLE 8

Ointment

"HIBIS WAKO™", a carboxyvinyl polymer, produced by Wako Pure Chemicals, Tokyo, Japan, and "TREHA®", a high-purity trehalose free of pyrogen, produced by Hayashibara Co. Ltd., Okayama, Japan, were respectively dissolved in sterilized distilled water to give respective concentrations of 1.4% (w/w) and 2.0% (w/w). The resulting mixture was mixed to homogeneity with an adequate amount of a physiologically active complex obtained by the method in Example 2 and adjusted to pH 7.2 to obtain a paste containing about five micrograms of the complex per one gram of the paste.

The product with a satisfactory extendibility and stability is useful as an ointment to treat and/or prevent susceptive diseases including malignant tumors, viral disease, bacterial infections, and immunopathies.

EXAMPLE 9

Tablet

"FINETOSE®", an anhydrous crystalline maltose powder produced by Hayashibara Co. Ltd., Okayama, Japan, was mixed to homogeneity with an adequate amount of a physiologically active complex obtained by the method in Example 2, and the mixture was tabletted in usual manner to obtain a tablet containing about one microgram of the complex per tablet, about 200 mg weight.

The product with a satisfactory swallowability and stability is useful as a tablet to treat and/or prevent susceptive diseases including malignant tumors, viral disease, bacterial infections, and immunopathies.

EXAMPLE 10

Preparation of Protein with TNF Activity

Using a clone obtained in the Example 1, a part of a DNA encoding the protein with the highest possible TNF-activity was amplified in the presence of the oligonucleotides represented by SEQ ID NOs:10 and 11 as primers, and the resulting amplified DNA having the nucleotide sequence represented by SEQ ID NO:13 was introduced into a plasmid vector, "pUC18", a trade name of and produced by Takara Shuzo, Co., Ltd. Tokyo, Japan. Then, according to conventional manner, the resulting plasmid vector was introduced into BL21DE3 strain, a microorganism of the species *Escherichia coli*, followed by culturing the resulting transformant and then purifying the resulting culture using methods such as ion-exchange chromatography and gel filtration chromatography to collect a protein having the amino acid sequence represented by SEQ ID NO:14.

A part of the protein thus obtained was sampled and subjected to SDS-PAGE in the presence of 2-mercaptoethanol and revealed to have a main band at around 17,000 daltons. Measurement of free amino acids of the protein in this example by conventional fluorescamine method revealed that the protein had one free amino group per molecule. According to conventional manner, the cytotoxicity of the protein was assayed by a bioassay using L-M cells as a target cell and revealed that the $IC_{50}$ of the protein was 0.03 ng/ml, substantially more than five times of that of 0.17 ng/ml for a human recombinant TNF as a control. These results show that the protein in this example has a replacement of six lysines among the seven amino acids, excluding the amino acid at the N-terminus, having free amino groups in TNF, with other amino acids having no free amino group, differs from TNF in several constituent amino acids of TNF, and exerts higher level of cytotoxicity against target cells of TNF.

EXAMPLE 11

Preparation of Physiologically Active Complex

A protein having TNF activity, obtained by the method in Example 10, was dissolved in aqueous phosphate buffered saline (pH 8.5) to give a concentration of 0.1 to 1 mg/ml and admixed with methoxypolyethyleneglycol as a high molecular substance having an average molecular weight of 5,000 daltons, which had been activated by the addition of monomethoxypolyethyleneglycol-N-succinimidylpropionate in an amount of five times of the protein by molar ratio, followed by reacting the mixture at 37° C. for 30 min. Thereafter, to the resulting mixture was added ε-aminocaproic acid in an amount of 10-times of the high molecular substance by molar ratio and allowed to stand for a while before terminating the reaction. The reaction mixture was then purified by conventional method using gel filtration chromatography to obtain a homogeneous physiologically active complex in which polyethylene glycol bound to the N-terminus of a proteinaceous part of the complex and had substantially no nonuniformity in molecular level.

The complex thus obtained exhibited a main peak at around 24,000 daltons on SDS-PAGE in the presence of 2-mercaptoethanol. When assayed for cytotoxicity by the above method using L-M cells as a target cell, the complex in this example had a cytotoxicity activity ($IC_{50}$) of about 60% of that of the human TNF obtained by the method in Example 10 and of about 340% of that of the TNF activity of the control.

EXAMPLE 12

Antitumor Action

According to usual manner, BALB/c female mice (4-weeks-old, 20 g weight each), which had been inoculated with meth A cells, ATCC 63181, a murine sarcoma, were divided into groups consisting of three heads per group and then injected into their tail veins with a physiological saline containing a physiologically active complex obtained by the method in Example 10, a protein with TNF activity obtained by the method in Example 1, or a recombinant human TNF at the doses in Table 2. At 24 hours after the administrations, the mice were examined for occurrence of hemorrhagic necrosis and sudden death, and measured for diameter of tumors at prescribed time intervals, followed by calculating the tumor volume according to the method described by Keisuke Haranaka in *International Journal of Medicine*, Vol.34, pp. 263–267 (1984). The anti-tumor effects (%) of the samples tested were calculated by comparing the tumor volumes of the mice, received with the samples, with those of the control mice injected with only physiological saline on day 20th after the transplantation of tumor cells. The results are in Table 2.

TABLE 2

| Sample | Dose (µg/head) | Sudden death (%) | Antitumor effect (%) |
| --- | --- | --- | --- |
| Recombinant human TNF | 10 | 100 | — |
|  | 3 | 0 | 10 |
| Protein obtained by | 10 | 100 | — |
| the method in Example 10 | 1 | 0 | 70 |
| Physiologically active | 10 | 0 | — |
| complex obtained by the method in Example 11 | 1 | 0 | 100 |

Note:
In the table, the symbol "—" means that it was not experimented.

As evident from the results in the Table 2, the mice, adiministered with either the protein obtained by the method in Example 10 or the recombinant human TNF, induced hemorrhagic necrosis within 24 hours after the administration of 10 µg/head, and all the mice died suddenly. When the dose of the protein or the recombinant human TNF was lowered stepwisely, the sudden death of mice could be avoided but no complete reduction of tumor mass was observed, and most of the mice died within 40 days after the administrations. While there were found no sudden death in the group administered with the physiologically active complex of the present invention even when administered at a dose of 10 μg/head, but found a significant antitumor effect even when administered at a dose of 1 μg/head. The data shows that the physiologically active complex of the present invention effectively elicits the antitumor effect of proteins having TNF activity and also significantly lowers the side effects of TNF.

EXAMPLE 13

In vivo Dynamics

Figure 3:
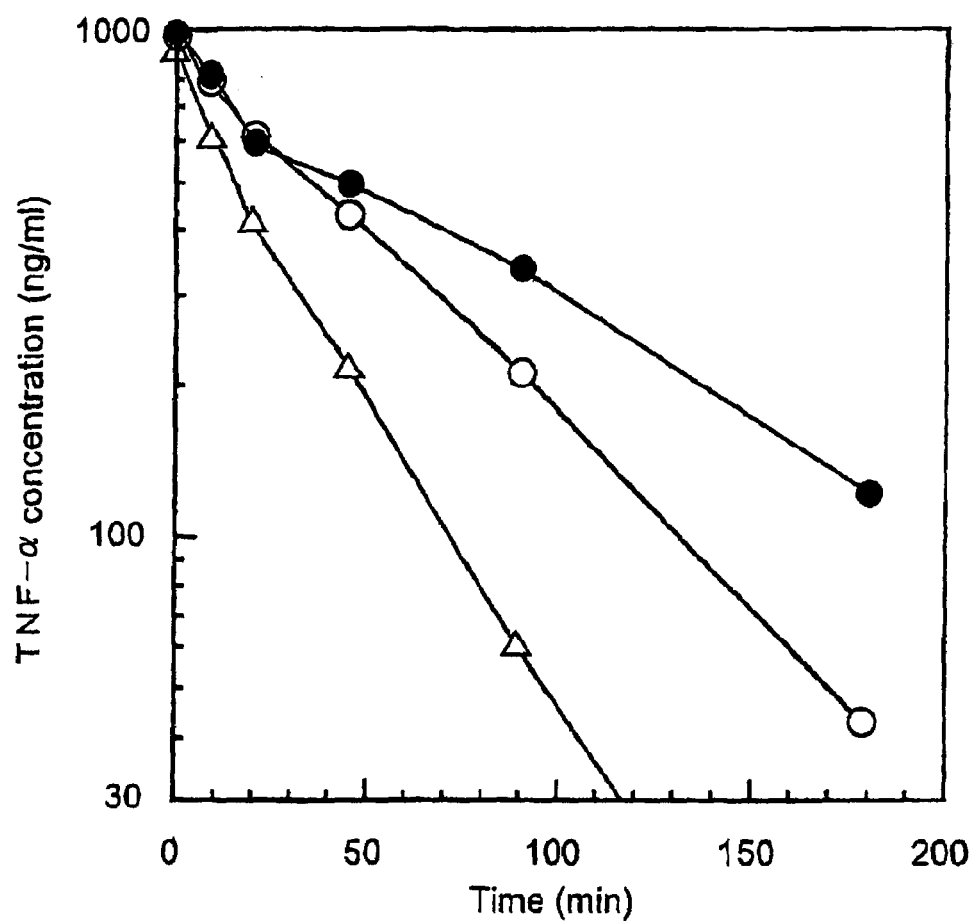
FIG. 3 shows in vivo dynamics of the physiologically active complex of the present invention in Example 11, containing a polypeptide having amino acid sequence described in SEQ ID NO:14 and a control substance.

The physiologically active complex obtained by the method in Example 11 was diluted with physiological saline to give a concentration of 5 μg/ml and injected into tail veins of BALB/c mice at a dose of 200 μl/head. Thereafter, the mice were sampled their blood at a prescribed time interval over three hours, and the serum level of the complex was assayed using a neutralizing antibody. In parallel, systems as controls, where a recombinant human TNF or a protein obtained by the method in Example 10 was administered to the target cell in place of the physiologically active complex, were respectively provided and treated similarly as above. The results are in FIG. 3. In FIG. 3, the systems administered with the physiologically active complex, the recombinant human TNF, and the protein obtained by the method in Example 10 were respectively expressed with the symbols "○", "●" and "Δ".

As evident from the results in FIG. 3, in the control systems, the serum levels of the recombinant human TNF and the protein instantly decreased just after the administrations and lowered to about 10% with respect to their initial levels at three hours after the administrations. While the system with the physiologically active complex of the present invention still had a residual cytotoxic activity of at least 10% with respect to the initial level. The data indicates that the physiologically active complex of the present invention has superior in viva dynamics and stays loner in living bodies as compared with conventional TNF and mutants thereof having no high molecular substance part at the N-terminus of TNF.

EXAMPLE 14

Acute Toxicity

According to conventional manner, mice aged eight weeks were percutaneously, orally, or peritoneally administered with the physiologically active complex of the present invention obtained by the method in Example 11, revealing that the $LD_{50}$ of the complex was 1 mg/kg body weight or more independently of its administration routes. This means that the physiologically active complex of the present invention can be incorporated into pharmaceuticals directed to be administered to humans with lesser side effects.

EXAMPLE 15

Liquid

A physiologically active complex, obtained by the method in Example 11, was dissolved in physiological saline containing one percent (w/w) of human serum albumin as a stabilizer to give a concentration of one milligram per milliliter, followed by filtering the solution with a membrane for sterilization in usual manner to obtain a liquid.

The product with a satisfactory stability is useful as an injection, ophthalmic solution, or nasal drop to treat and/or prevent susceptive diseases including malignant tumors, viral disease, bacterial infections, and immunopathies.

EXAMPLE 16

Dried Injection

One hundred milligrams of a physiologically active complex, obtained by the method in Example 11, was dissolved in 100 ml of physiological saline containing one percent (w/w) of a purified human gelatin as a stabilizer, and then the resulting solution was membrane filtered for sterilization in usual manner. One milliliter aliquots of the filtrate were distributed into vials and lyophilized, followed by sealing the vials to obtain a dried injection.

The product with a satisfactory stability is useful as an injection, ophthalmic solution, or nasal drop to treat and/or prevent susceptive diseases including malignant tumors, viral disease, bacterial infections, and immunopathies.

EXAMPLE 17

Ointment

"HIBIS WAKO™", a carboxyvinyl polymer, produced by Wako Pure Chemicals, Tokyo, Japan, and "TREHA®", a high-purity trehalose free of pyrogen, produced by Hayashibara Co. Ltd., Okayama, Japan, were respectively dissolved in sterilized distilled water to give respective concentrations of 1.4% (w/w) and 2.0% (w/w). The resulting mixture was mixed to homogeneity with an adequate amount of a physiologically active complex obtained by the method in Example 2 and adjusted to pH 7.2 to obtain a paste containing about five micrograms of the complex per one gram of the paste.

The product with a satisfactory extendibility and stability is useful as an ointment to treat and/or prevent susceptive diseases including malignant tumors, viral disease, bacterial infections, and immunapathies.

EXAMPLE 18

Tablet

"FINETOSE®", an anhydrous crystalline maltose powder produced by Hayashibara Co. Ltd., Okayama, Japan, was mixed to homogeneity with an adequate amount of a physiologically active complex obtained by the method in Example 2, and the mixture was tabletted in usual manner to obtain a tablet containing about one microgram of the complex per tablet, about 200 mg weight.

The product with a satisfactory swallow ability and stability is useful as a tablet to treat and/or prevent susceptive diseases including malignant tumors, viral disease, bacterial infections, and immunopathies.

As explained above, the physiologically active complex, which comprises a proteinaceous part with TNF activity and a high molecular part bound artificially to the N-terminus of the protein, has a satisfactory in vivo dynamics and keeps the desired initial serum level for a relatively long period of time even when injected to living bodies. Thus, the agent for susceptive diseases comprising the physiologically active complex as an effective ingredient according to the present invention has a variety of uses in the field of pharmaceuticals such as antitumor agents, antiviral agents, anti-infection agents, and agents for immunopathies.

Since the physiologically active complex of the present invention has a high molecular substance which binds to only the N-terminus of a proteinaceous part with TNF activity, the complex, in theory, has the merit that it should not be anxious for nonuniformity with respect to molecularsize-distribution that has been pointed out in conventionally known complexes having lymphokine activities. When proteins, in which the amino acids with free amino groups in TNF, excluding the one positioned at the N-terminus, are replaced with other amino acids with no free amino group, are used as the protein which constitutes the physiologically active complex of the present invention, a physiologically active complex in which a high molecular substance binds only to the N-terminus of TNF is obtained in a relatively high yield. In this case, the use of any of amino acids with no free amino group, for example, asparagine, alanine, arginine, serine, threonine, proline, methionine, and leucine, provides the physiologically active complex which retains the desired physiological actions of TNF in whole or in a quite high level in a roughly theoretical yield.

The present invention with such outstanding effects is a significant invention that will greatly contribute to this art.

While there has been described what is at present considered to be the preferred embodiments of the invention, it will be understood the various modifications may be made therein, and it is intended to cover in the appended claims all such modifications as fall within the true spirits and scope of the invention.

We claim:

1. A physiologically active complex, which comprises a proteinaceous part having a N-terminus and a water soluble polymer bound covalently to the N-terminus of the proteinaceous part, wherein said proteinaceous part comprises the amino acid sequence of SEQ ID NO: 2 where Xaa is the same or a different member selected from the group consisting of asparagine, alanine, arginine, serine, threonine, proline, methionine, and leucine, and has a TNF-α activity.

2. The complex of claim 1, wherein said water-soluble polymer has a molecular weight of 500–50,000 daltons.

3. The complex of claim 1, wherein said water-soluble polymer is polyethylene glycol.

4. A method for treating tumors, which comprises a step of administrating the complex of claim 1 to a patient in needs thereof.

5. The physiologically active complex of claim 1, wherein said proteinaceous part comprises the amino acid sequence of SEQ ID NO:3 or NO:14.

* * * * *